United States Patent
Ni et al.

(10) Patent No.: US 9,440,226 B2
(45) Date of Patent: Sep. 13, 2016

(54) METHOD FOR PREPARING METHYL ACETATE

(71) Applicant: DALIAN INSTITUTE OF CHEMICAL PHYSICS, CHINESE ACADEMY OF SCIENCES, Liaoning (CN)

(72) Inventors: Youming Ni, Liaoning (CN); Wenliang Zhu, Liaoning (CN); Hongchao Liu, Liaoning (CN); Yong Liu, Liaoning (CN); Zhongmin Liu, Liaoning (CN); Shuanghe Meng, Liaoning (CN); Lina Li, Liaoning (CN); Shiping Liu, Liaoning (CN); Hui Zhou, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 0 days.

(21) Appl. No.: 14/650,589

(22) PCT Filed: Jan. 28, 2014

(86) PCT No.: PCT/CN2014/000124
§ 371 (c)(1),
(2) Date: Jun. 9, 2015

(87) PCT Pub. No.: WO2014/101897
PCT Pub. Date: Jul. 3, 2014

(65) Prior Publication Data
US 2015/0298108 A1    Oct. 22, 2015

(30) Foreign Application Priority Data

Dec. 25, 2012 (CN) .......................... 2012 1 0571057
Dec. 25, 2012 (CN) .......................... 2012 1 0571065
Dec. 25, 2012 (CN) .......................... 2012 1 0571440

(51) Int. Cl.
*B01J 31/02* (2006.01)
*B01J 29/18* (2006.01)
*C07C 67/37* (2006.01)
*B01J 37/02* (2006.01)

(52) U.S. Cl.
CPC ............. *B01J 31/0244* (2013.01); *B01J 29/18* (2013.01); *B01J 31/0237* (2013.01); *B01J 31/0238* (2013.01); *C07C 67/37* (2013.01); *B01J 37/0203* (2013.01); *B01J 2229/34* (2013.01)

(58) Field of Classification Search
CPC ............. B01J 31/0244; B01J 31/0237; B01J 31/0238; B01J 29/18; B01J 2229/34; B01J 37/0203; C07C 67/37
See application file for complete search history.

(56) References Cited

U.S. PATENT DOCUMENTS

2007/0238897 A1* 10/2007 Cheung ................... C07C 51/09
560/232

FOREIGN PATENT DOCUMENTS

EP          1985606          * 10/2008

OTHER PUBLICATIONS

Li, Xingang, et al., "Direct Synthesis of Ethanol from Dimethyl Ether and Syngas over Combined H-Mordenite and Cu/ZnO Catalysts", ChemSusChem, vol. 3, pp. 1192-1199, 2010.
Cheung, Patricia, et al., "Site requirements and elementary steps in dimethyl ether carbonylation catalyzed by acidic zeolites", Journal of Catalysis, vol. 245, pp. 110-123, 2007.
Bhan, Aditya, et al., "Specificity of Sites within Eight-Membered Ring Zeolite Channels for Carbonylation of Methyls to Acetyls", Journal of the American Chemical Society, vol. 129, pp. 4919-4924, 2007.
Liu, Junlong, et al., "Stability Enhancement of H-Mordenite in Dimethyl Ether Carbonylation to Methyl Acetate by Pre-adsorption of Pyridine", vol. 31, No. 7, pp. 729-738, 2010.

* cited by examiner

*Primary Examiner* — Shailendra Kumar
(74) *Attorney, Agent, or Firm* — Nath, Goldberg & Meyer; Joshua B. Goldberg; Tanya E. Harkins

(57) ABSTRACT

The present invention provides a method for preparing methyl acetate, in which a feed gas containing an organic amine, dimethyl ether, carbon monoxide and optional hydrogen gas goes through a reactor loaded with a H-type mordenite catalyst, to produce methyl acetate; wherein said H-type mordenite catalyst is a H-type mordenite catalyst with adsorption of an organic amine. The method in the present invention improves the catalyst stability and prolongs the catalyst life, by using the H-type mordenite catalyst with adsorption of an organic amine as the catalyst and adding the organic amine in the feed gas to replenish the organic amine desorbed from the catalyst during the reaction.

12 Claims, No Drawings

METHOD FOR PREPARING METHYL ACETATE

This is a National Phase Application filed under 35 U.S.C. 371 as a national stage of PCT/CN2014/000124, filed Jan. 28, 2014, an application claiming the benefit of Chinese Application No. 201210571065.2, filed Dec. 25, 2012, Chinese Application No. 201210571440.3, filed Dec. 25, 2012 and Chinese Application No. 201210571057.8, filed Dec. 25, 2012, the contents of each of which is hereby incorporated by reference in its entirety.

TECHNICAL FIELD

The present invention relates to a method for preparing methyl acetate, and particularly relates to a method for preparing methyl acetate by the carbonylation of dimethyl ether.

BACKGROUND

Methyl acetate is an important organic chemical material and solvent. Methyl acetate can be used to produce acetic acid and its derivatives, such as acetic anhydride, vinyl acetate and the like. In present industrial production, acetic acid has been mainly prepared by the Monsanto and BP homogeneous carbonylation of methanol, in which the noble metal catalysts containing Rh or Ir and the corrosive catalyst promoters $CH_3I$ have been used [J. Catal. 245 (2007) 110~123]. Methyl acetate can be used for producing ethanol by the hydrogenation reduction [ChemSusChem 3 (2010) 1192~1199]. The octane value of ethanol is higher than gasoline, and ethanol can burn completely in the combustion engine so that ethanol itself or its mixture with gasoline both can be used as the automobile fuels. Now ethanol gasoline with the ethanol content range from 5% to 85% has been commercially used. Mixing ethanol into gasoline also can reduce the greenhouse gas emission. Currently ethanol has been industrially produced by two main ways which are the biological fermentation of corn or sugarcane and the hydration of ethylene. Biological fermentation to produce ethanol generally only can produce a low concentration ethanol which is about 14%. To obtain the fuel ethanol, the usage of rectification process became necessary, which need the heavy investment and the high energy consumption. Besides ethanol productivity of the biological fermentation is limited to avoid threatening food security because the biological fermentation is at the expense of economic crops, such as grain. The hydration of ethylene is losing its economic competitiveness with the exhaustion of oil resources and the price rise of ethylene, since ethylene is obtained mainly from petrochemical industry. In addition, methyl acetate can be used as a green solvent which is widely applied in the field of textile, spices, medicine, food and the like. Methyl acetate also can be obtained by the carbonylation of dimethyl ether and carbon monoxide, and dimethyl ether can be prepared by the dehydration of methanol or the one-step synthesis from syngas, so methyl acetate can be seen as a derivative of syngas. Industrial synthesis technology of syngas is very mature by the gasification of non-petroleum sources, such as coal, natural gas, biomass and the like.

So far, among the catalysts for preparing methyl acetate by the carbonylation of dimethyl ether which have been reported, mordenite with 8-membered ring and 10-membered ring is the most studied and the most active. Iglesia et al. found that the active centers of catalysis carbonylation locate at Bronsted acid sites of 8-membered ring [J. Am. Chem. Soc. 129 (2007) 4919~4924] and the selectivity for methyl acetate was higher than 99%, while they did not study the life and inactivation of the catalysts in details. The research work of Wenjie Shen et al. indicated that the stability of the carbonylation of dimethyl ether could be improved significantly by pre-adsorbing pyridine in mordenite [Chin. J. Catal. 31 (2010) 729~738], and the yield of methyl acetate was kept at about 30% after reacting for 48 h at 200° C. Pyridine located in 12-membered ring restricts the generation of carbon deposits in 12-membered ring, and acid sites of 8-membered ring are not affected. However, pyridine adsorbed in mordenite will desorb slowly under the reaction conditions, resulting in the decline of catalyst activity, catalyst stability and catalyst life with the slow increase of carbon deposits, which seriously restrict the large-scale application in industrial production.

DISCLOSURE

An object of the present invention is to provide a method for preparing methyl acetate, which is characterized in that the catalyst is a H-type mordenite with adsorption of an organic amine, and the feed gas is a mixture gas containing an organic amine, dimethyl ether, carbon monoxide and optional hydrogen gas, and the feed gas goes through the catalyst to produce methyl acetate stably and efficiently under the reaction conditions. The present invention further improves the catalyst stability and drastically prolongs the catalyst life at the same time by adding an organic amine into the feed gas. In order to realize the above object, the present invention provides a method for preparing methyl acetate, in which a feed gas containing an organic amine, dimethyl ether, carbon monoxide and optional hydrogen gas goes through a reaction region loaded with a H-type mordenite catalyst, to produce methyl acetate at a reaction temperature range from 150° C. to 320° C., a reaction pressure range from 0.1 MPa to 8 MPa and a gas hourly space velocity range from 500 $h^{-1}$ to 10000 $h^{-1}$; said reaction region contains one reactor or reactors which are connected in series or in parallel; said organic amine is at least one selected from pyridines amines, aromatic amines or alicyclic amines; said H-type mordenite catalyst is a H-type mordenite catalyst with adsorption of an organic amine; said H-type mordenite is acid mordenite; in said feed gas, the molar ratio range of carbon monoxide to dimethyl ether is from 1:1 to 45:1, and the molar ratio range of the organic amine to dimethyl ether is from 0.00001:1 to 0.2:1, and the molar ratio range of hydrogen gas to dimethyl ether is from 0:1 to 20:1.

As a preferred embodiment, the reaction temperature range is from 200° C. to 280° C.

As a preferred embodiment, the reaction pressure range from 3 MPa to 5 MPa.

As a preferred embodiment, the gas hourly space velocity range from 2000 $h^{-1}$ to 5000 $h^{-1}$.

As a preferred embodiment, the molar ratio range of carbon monoxide to dimethyl ether is preferable from 2:1 to 10:1.

As a preferred embodiment, the molar ratio range of hydrogen gas to dimethyl ether is preferable from 1:1 to 10:1.

As a preferred embodiment, in said feed gas, the molar ratio range of the organic amine to dimethyl ether is from 0.0001:1 to 0.01:1.

As a preferred embodiment, said H-type mordenite catalyst with adsorption of an organic amine is prepared by the steps as follows: the H-type mordenite is loaded in a reactor, and then at an adsorption temperature range from 90° C. to 420° C., a mixture gas is introduced into the reactor, which contains the organic amine and at least one selected from carbon monoxide, hydrogen gas, air, nitrogen gas, helium gas or argon gas; after the saturated adsorption of the organic amine, the reactor is purged by at least one selected from carbon monoxide, hydrogen gas, air, nitrogen gas, helium gas or argon gas for a time range from 0.5 hour to 6 hours at the adsorption temperature, to obtain said H-type mordenite catalyst with adsorption of the organic amine.

As a preferred embodiment, a preferable adsorption time range is from 0.5 hour to 48 hours.

As a preferred embodiment, a preferable adsorption temperature range is from 160° C. to 320° C.

As a preferred embodiment, the atom ratio of silicon to aluminum in said H-type mordenite catalyst is at a range from 4:1 to 60:1; and the atom ratio of silicon to aluminum in said H-type mordenite catalyst is at a further preferable range from 5:1 to 20:1.

As a preferred embodiment, said pyridines amine is at least one selected from pyridine or the substituted pyridines. As a preferred embodiment, said substituted pyridines are the compounds which one, two or three of five H atoms in the pyridine ring is respectively substituted by the substituent group selected from F, Cl, Br, I, $CH_3$, $CH_3CH_2$, $CF_3$ or $NO_2$.

As a preferred embodiment, said aromatic amine is at least one selected from phenylamine or the substituted phenylamines.

As a preferred embodiment, said substituted phenylamines are the compounds which one, two, three, four, five, six or seven of seven H atoms composed of five H atoms in the benzene ring and two atoms in the amine group is respectively substituted by the substituent group selected from F, Cl, Br, I, $CH_3$, $CF_3$ or $CH_3CH_2$.

As a preferred embodiment, said alicyclic amines are the organic amines containing ring structure in their molecular structure, which are formed through the substitution of at least one H atom of ammonia molecule by aliphatic group.

As a preferred embodiment, the N atom of amino group in said alicyclic amines can be located out the ring, such as

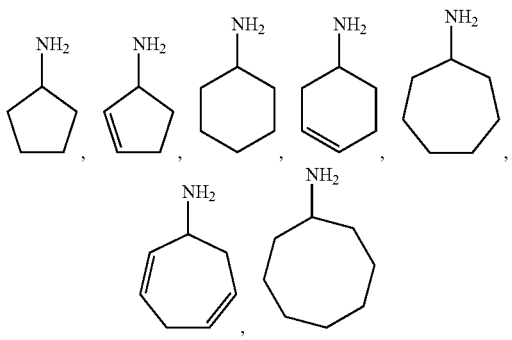

and the like; and the N atom of amino group in said alicyclic amines can be located at the ring, such as

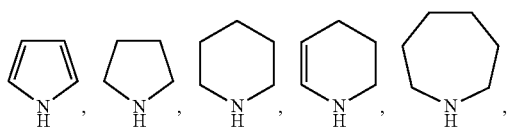

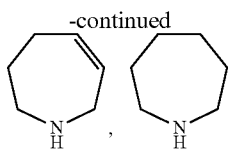

and the like.

As a preferred embodiment, said alicyclic amine is at least one selected from the alicyclic amines with the number of ring members ranging from 5 to 8 or the substituted alicyclic amines with the number of ring members ranging from 5 to 8.

As a preferred embodiment, said alicyclic amine is at least one selected from cyclohexylamine

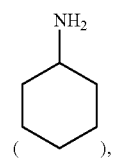

piperidine

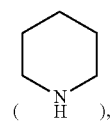

the substituted cyclohexylamines or the substituted piperidines.

As a preferred embodiment, said substituted cyclohexylamines are the compounds which at least one of thirteen H atoms in the cyclohexylamine is respectively substituted by the substituent group selected from F, Cl, Br, I, $CH_3$, $CF_3$, $CH_3CH_2$ or $NO_2$.

As a preferred embodiment, said substituted piperidines are the compounds which at least one of eleven H atoms in the piperidine is respectively substituted by the substituent group selected from F, Cl, Br, I, $CH_3$, $CF_3$, $CH_3CH_2$ or $NO_2$.

As a preferred embodiment, the organic amine adsorbed in said H-type mordenite catalyst is same as the organic amine in said feed gas, or the organic amine adsorbed in said H-type mordenite catalyst is different from the organic amine in said feed gas.

As a preferred embodiment, the organic amine adsorbed in said H-type mordenite catalyst is at least one selected from pyridine, 2-methylpyridine, phenylamine, 4-methylaniline, cyclohexylamine or piperidine.

As a preferred embodiment, the organic amine in said feed gas is at least one selected from pyridine, 2-methylpyridine, phenylamine, 4-methylaniline, cyclohexylamine or piperidine.

As a preferred embodiment, the organic amine adsorbed in said catalyst is pyridine and/or 2-methylpyridine; the organic amine in said feed gas is pyridine and/or 2-methylpyridine.

As a preferred embodiment, the organic amine adsorbed in said catalyst is phenylamine and/or 4-methylaniline; the organic amine in said feed gas is phenylamine and/or 4-methylaniline.

As a preferred embodiment, the organic amine adsorbed in said catalyst is cyclohexylamine and/or piperidine; the organic amine in said feed gas is cyclohexylamine and/or piperidine.

As a preferred embodiment, the organic amine in said feed gas is the fresh organic amine or the recycled organic amine obtained in the process of the product separation.

As a preferred embodiment, said reactor is a continuous flow fixed bed reactor, a moving bed reactor or a fluid bed reactor. A person skilled in the art can choose the appropriate amount, type and connection mode of the reactors according to the demands of industrial production.

As a preferred embodiment, the product methyl acetate can be used for producing ethanol by the hydrogenation reduction.

In the present invention, said pyridines amines can be described as pyridines compounds, including aminopyridines, bromopyridines, methylpyridines, iodopyridines, chloropyridines, nitropyridines, hydroxypyridines, benzylpyridines, ethylpyridines, cyanopyridines, fluoropyridines, dihydropyridines and other alkylpyridines and halogenated pyridines, and the like.

According to the common knowledge in the art, said H-type mordenite is the mordenite with acidity.

According to the common knowledge in the art, said bromopyridines are such as 2-fluoro-5-bromopyridine, 2-amino-3-iodo-5-bromopyridine, 4-bromopyridine hydrochloride, 2-chloro-4-bromopyridine, 4-amino-3-bromopyridine, 2-hydrazino-5-bromopyridine, 2-fluoro-3-bromopyridine, 2,3,5-tribromopyridine, 5-bromopyridine-2-carboxylic acid methyl ester, 2-fluoro-4-methyl-5-bromopyridine, 2-acetyl-5-bromopyridine, 3,5-dibromopyridine, 2,3-dibromopyridine, 4-bromopyridine-2-methanol, 2,4-dibromopyridine, 2,6-dimethyl-3-bromopyridine, 2,6-dibromopyridine, 2,5-dichloro-3-bromopyridine, and the like.

According to the common knowledge in the art, said iodopyridines are such as 4-(BOC-amino)-3-iodopyridine, 2-amino-3-methyl-5-iodopyridine, 2-bromo5-iodopyridine, 5-bromo-2-iodopyridine, 2-amino-5-chloro-3-iodopyridine, 2-chloro-4-iodopyridine-3-formaldehyde, 3-amino-4-iodopyridine, 2-fluoro-3-formyl-4-iodopyridine, 3-fluoro-4-iodopyridine, 2,6-dichloro-4-iodopyridine, 2-iodopyridine, 2-chloro-5-(trifluoromethyl)-4-iodopyridine, 3-bromo-5-iodopyridine, 2,5-diiodopyridine, 2-bromo-4-iodopyridine, 4-amino-3-iodopyridine, 2-amino-3-iodopyridine, 2-fluoro-3-iodopyridine, and the like.

According to the common knowledge in the art, said nitropyridines are such as 2-amino-4-methyl-5-nitropyridine, 2,4-dichloro-6-methyl-3-nitropyridine, 3-chloro-2-nitropyridine, 2-fluoro-3-nitropyridine, 2,4-dichloro-5-nitropyridine, 2-methoxy-4-methyl-5-nitropyridine, 2,6-dichloro-3-nitropyridine, 4-chloro-3-nitropyridine, 3-ethoxy-2-nitropyridine, 3,5-dimethyl-2-hydroxymethyl-4-nitropyridine, 2,6-dibromo-3-nitropyridine, 1-(5-nitropyridin-2-yl)piperazine, 4-methoxy-3-nitropyridine, 3-bromo-4-nitropyridine N-oxide, 5-bromo-2-nitropyridine, 2,5-dibromo-3-nitropyridine, 3-amino-2-nitropyridine, 5-methyl-2-amino-3-nitropyridine, and the like.

According to the common knowledge in the art, said methylpyridines are such as 2,5-dibromo-3-methylpyridine, 2-fluoro-6-methylpyridine, 2-(chloromethyl)-4-methoxy-3,5-dimethylpyridine, 2-amino-3-bromo-6-methylpyridine, 2-methyl-6-(trifluoromethyl)pyridine-3-carbonyl chloride, 6-bromo-3-(hydroxymethyl)pyridine, 2-bromo-4-methylpyridine, 2-chloromethyl-4-(3-methoxypropoxy)-3-methyl-pyridin, 3-(chloromethyl)pyridine hydrochloride, 2-amino-5-bromo-4-methylpyridine, 2-methoxy-5-(trifluoromethyl) pyridine, 5-cyano-2-methylpyridine, 3-formyl-6-methylpyridine, 2,5-dibromo-6-methylpyridine, 5-bromo-2-(hydroxymethyl)pyridin, 3-amino-2-methylpyridine, 2-fluoro-6-(trifluoromethyl)pyridine, 3-(trifluoromethyl)pyridine, and the like.

According to the common knowledge in the art, said ethylpyridines are such as 1-ethyl-1,2-dihydro-6-hydroxy-4-methyl-2-oxo-3-pyridinecarboxamide, 3-(2-aminoethyl) pyridine, 3-(2-chloroethyl)-6,7,8,9-tetrahydro-2-methyl-4H-pyrido[1,2-a]pyrimidin-4-ketone, 2-bromo-4-ethylpyridine, 2-(2-aminoethyl)pyridine, 2-amino-4-ethylpyridine, diethyl (3-pyridyl)-borane, 5-{4-[2-(5-ethyl-2-pyridyl)-ethoxy]-benzyl}-2-imido-4-thiazolidone, 1-ethylpyridine bromide, 1-ethylpyridine chloride, 2-amino-4,7-dihydro-5H-thieno[2,3-C]pyridine-3,6-dicarboxylic acid 6-tert butyl ester, 3-(2-chloroethyl)-6,7,8,9-tetrahydro-9-hydroxy-2-methyl-4H-pyridine[1,2-a]pyrimidine-4-ketone, 1-dimethylcarbamyl-4-(2-sulfoethyl)pyridinium hydroxide inner salt, 5-ethyl-2-pyridineethanol, 2-ethyl-6-methyl-3-pyridinol, 5-ethylpyridine-2,3-dicarboxylic acid, 3-ethylpyridine, 2-hydroxyethyl pyridine, and the like.

According to the common knowledge in the art, said aminopyridines are such as 2,6-diaminopyridine, 2-chloro-4-aminopyridine, 2-acetamidopyridine, 3-chloro-2-aminopyridine, 4-(methylamino)pyridine, 2,6-dichloro-3-aminopyridine, 4-(3'-methylphenyl)amino-3-pyridinesulfonamide, 2-chloro-5-aminopyridine, 6-aminopicolinic acid methyl ester, 2-methoxy-6-(methylamino)pyridine, 2,4-diaminopyridine, 6-methoxypyridine-2,3-diamine dihydrochloride, 2-benzylaminopyridine, 3-aminopyridine-4-carboxylic acid ethyl ester, 3-methyl-4-aminopyridine, 2,6-dibromo-3-aminopyridine, 2-bromo-3-aminopyridine, 2-acetamido-5-aminopyridine, and the like.

According to the common knowledge in the art, said fluoropyridines are such as 2-fluoropyridine-5-carboxaldehyde, 2,6-difluoropyridine-3-boronic acid, 2-chloro-3-fluoropyridine-4-boronic acid, 2-methoxyl-3-bromo-5-fluoropyridine, 2-fluoropyridine-6-carboxylic acid, 5-chloro-2-fluoropyridine, 2-bromo-4-fluoropyridine, 3,5-dichloro-2,4,6-trifluoropyridine, 4-amino-3,5-dichloro-2,6-difluoropyridine, 2-amino-3-fluoropyridine, 2-fluoropyridine, 2-chloro-3-fluoropyridine, 2-chloro-3-nitro-5-fluoropyridine, 3-fluoropyridine-2-carboxylic acid, 3-chloro-2,4,5,6-tetrafluoropyridine, 4-bromo-2-fluoropyridine, 2-bromo-3-fluoropyridine, and the like.

According to the common knowledge in the art, said chloropyridines are such as 2-amino-6-chloropyridine, 2-[N,N-bis(trifluoromethanesulfonyl)amino]-5-chloropyridine, 2-amino-3-nitro-6-chloropyridine, 5-amino-2,3-dichloropyridine, 2-chloropyridine-4-boronic acid pinacol ester, 2,3-diamino-5-chloropyridine, 2-amino-3,5-dichloropyridine, 2-chloropyridine-N-oxide, 2-methoxy-3-bromo-5-chloropyridine, 2-amino-5-chloropyridine, 3-acetyl-2-chloropyridine, 2-methyl-6-chloropyridine, 4-amino-3,5-dichloropyridine, 6-chloropyridine-2-carboxylic acid, 2,6-dichloropyridine, 2-chloropyridine-5-sulfonyl chloride, 3,5-dichloropyridine-4-carboxylic acid, 3-amino-2,4-dichloropyridine, and the like.

According to the common knowledge in the art, said hydroxypyridines are such as 4-hydroxy-6-methyl-3-nitro-2-pyridino, 3-bromo-2-hydroxy-5-methylpyridine, 6-methyl-2-hydroxypyridine, 1,2-dimethyl-3-hydroxy-4-pyridone, 2-amino-3-hydroxypyridine, 2-hydroxy-4-(trifluoromethyl)pyridine, 2-hydroxy-5-iodopyridine, 2-hydroxy-4-methylpyridine, 2-hydroxy-5-methyl-3-nitropyridine, 2-hydroxy-6-methyl-5-nitropyridine, 2,6-dihydroxy-3,4-dimethylpyridine, 3-amino-4- hydroxypyridine, 2-hydroxy-3-nitropyridine, 2-hydroxypyridine, 3-chloro-2-hydroxy-5-nitropyridine, 2-hydroxypyridine-N-oxide, 4-hydroxy-3-methylpyridine, 2-bromo-6-hydroxypyridine, and the like.

According to the common knowledge in the art, said cyanopyridines are such as 3-cyano-6-trifluoromethylpyridine, 5-bromo-3-nitro-2-cyanopyridine, 2-amino-3-cyanopyridine, 3-nitro-2-cyanopyridine, 4-cyanopyridine, 3-cyano-2-fluoropyridine, 3-cyano-6-hydroxypyridine, 4-chloro-3-cyanopyridine, 3-cyano-4-methylpyridine, 3-amino-6-cyanopyridine, 2-cyano-5-hydroxypyridine, 2-cyano-3-fluoropyridine, 3-chloro-4-cyanopyridine, 4-cyanopyridine N-oxide, 2-chloro-3-cyanopyridine, 3-amino-4-cyanopyridine, 2-cyanopyridine-5-boronic acid pinacol ester, 5-bromo-2-cyanopyridine, and the like.

According to the common knowledge in the art, said dihydropyridines are such as 2,3-dihydropyrido[2,3-d][1,3]oxazol-2-one, chelidamic acid, 6,7-dihydro-5H-pyrrolo[3,4-b]pyridine, 5-bromo-2,3-dihydro-1H-pyrrolo[2,3-B]pyridine, methyl 2-oxo-1,2-dihydro-3-pyridinecarboxylate, tert-butyl 2,4-dichloro-5,6-dihydropyrido[3,4-D]pyrimidine-7(8H)-carboxylate, 2,3-dihydro-1,4-dioxino[2,3-b]pyridine, 9-methyl-3,4-dihydro-2H-pyrido[1,2-A]pyrimidin-2-one, N-cbz-3,6-dihydro-2H-pyridine-4-boronic acid pinacol ester, 3,4-dihydro-2H-pyrido[1,2-D]pyrimidin-2-one, 4,5-dihydro-4-oxofuro[3,2-C]pyridine, 6,7-dihydro-5H-1-pyridin-5-one, 6,7-dihydro-5H-pyrrolo[3,4-b]pyridine dihydrochloride, diethyl 1,4-dihydro-2,4,6-trimethyl-3,5-pyridinedicarboxylate, 1-methyl-6-oxo-1,6-dihydropyridine-3-carboxylic acid, tert-butyl 2-chloro-7,8-dihydropyrido[4,3-D]pyrimidine-6(5H)-carboxylate, 3-(1-acetyl-1,4-dihydropyridin-4-yl)-1H-indole, 2-chloro-6,7-dihydro-5H-pyrrolo[3,4-B]pyridine, and the like.

According to the common knowledge in the art, said benzylpyridines are such as 2-benzylpyridine, 4-(4-nitrobenzyl)pyridine, 2-(4-chlorobenzyl)pyridine, 4-benzylpyridine, 1-benzylpyridinium-3-carboxylate, 6-benzyl-2,4-dichloro-5,6,7,8-tetrahydropyrido[4,3-D]pyrimidine, 7-benzyl-4-chloro-5,6,7,8-tetrahydropyrido[3,4-D]pyrimidine, 4-(4-chlorobenzyl)pyridine, 7-benzyl-5,6,7,8-tetrahydropyrido[3,4-D]pyrimidin-4(3H)-one, dinitrobenzylpyridine, 3-benzylpyridine, 6-benzyl-5,7-dioxooctahydropyrrolo[3,4-B]pyridine, [(4-chloro-benzyl)pyridine-3-yl]methylamine, [(4-fluoro-benzyl)-pyridin-3-yl]methylamine, 7-benzyl-5,6,7,8-tetrahydropyrido[3,4-D]pyrimidine-2,4(1H,3H)-dione, 1-(4-nitrobenzyl)-4-(4-diethylaminophenylazo)pyridinium bromide, 2-amino-3-nitro-6-(4-fluorbenzylamino)pyridine, (benzylpyridin-2-yl)methylamine, and the like.

A person skilled in the art can choose the appropriate pyridines compounds according to the demands of industrial production.

According to the common knowledge in the art, said aromatic amines are the aromatic compounds whose molecular structure contain one or more benzene rings and the benzene ring is connected with N of amino group. Common arylamines are such as 4-isopropylaniline, N-methylaniline, 2,4,6-trichloroaniline, 2,4-dinitroaniline, 2-ethylaniline, 2-chloro-4-nitroaniline, N-ethylaniline, N,N-dimethylaniline, o-toluidine, m-phenylenediamine, diphenylamine, 2,6-dimethylaniline, 3-nitroaniline, 1-naphthylamine, N,N-diethylaniline, 4-methyl-2-nitroaniline, 4-nitroaniline, 3,3'-diaminobenzidine, 4-chloro-2,5-dimethoxyaniline, 4-fluoro-3-nitroaniline, 3-fluoro-N-methylaniline, 2,6-dinitroaniline, 2-fluoro-4-iodoaniline, 3-bromo-2,4,6-trimethylaniline, 2-bromo-4-chloroaniline, 2-tert-butylaniline, 2-chloro-4-nitro-6-bromoaniline, N-methyl-p-nitroaniline, 4-fluoro-2-nitroaniline, 4-bromo-2-methoxyphenylamine, 2'-bromo-4'-fluoroacetanilide, N-benzyl-N-ethyl-m-toluidine, 2-fluoro-6-methylaniline, N-methyl-o-toluidine, 2-fluoro-3-(trifluoromethyl)aniline, 3,5-dimethoxyaniline, 2-chloro-4-iodoaniline, 4-methyl-3-nitroaniline, 3-fluoro-4-methylaniline, 4-ethylaniline, 2-bromo-6-methylaniline, 4-butylaniline, N-isopropylaniline, 2-chloro-N-methylaniline, 2,6-dibromo-4-chloroaniline, 3-bromo-2-methylaniline, 2-iodo-4-chloroaniline, N-methyl-p-toluidine, 2-propylaniline, 4-methyl-3-(trifluoromethyl)aniline, 2-methyl-4-methoxyaniline, 3-(trifluoromethoxy)aniline, 2-(difluoromethoxy)aniline, 3-(difluoromethoxy)aniline, 2,5-dimethoxy-4-nitroaniline, 2,4-dichloro-6-nitroaniline, 4,5-difluoro-2-nitroaniline, 2-chloro-5-nitroaniline, o-aminoacetanilide, 5-methoxy-2-methylaniline, m-aminoacetanilide, 5-methyl-2-nitroaniline, 2,4-dimethoxyaniline, 2,4,5-trichloroaniline, 2-nitrodiphenylamine, 3,4,5-trimethoxyaniline, 3,5-di-tert-butylaniline, 2-bromoaniline, 2,4,6-tribromoaniline, 4-chloro-N-methylaniline, N,N-dimethyl-p-toluidine, 4-bromo-N,N-dimethylaniline, 4-hexylaniline, 3-iodo-4-methylaniline, 2-bromo-4-fluoro-6-methylaniline, 2-iodo-4-nitroaniline, 2,4-dibromo-6-nitroaniline, 2-bromo-6-chloro-4-(trifluoromethyl)aniline, 2,3,4-trifluoro-6-nitroaniline, 2,5-dibromoaniline, 2-aminodiphenylamine, 2-chloro-4,6-dinitroaniline, 4-iodoaniline, 2-iodoaniline, 4,5-dichloro-2-nitroaniline, 5-iodo-2-methylaniline, 2-bromo-4,6-dimethylaniline, 2-bromo-5-nitroaniline, 4-bromo-2,6-dichloroaniline, N-methyl-2-nitroaniline, 2-chloro-4-(trifluoromethoxy)aniline, 3-iodoaniline, 4-decylaniline, 2,6-diisopropylaniline, 3-fluoroacetanilide, 2,6-dichloro-4-(trifluoromethoxy)aniline, 3-ethylaniline, 2,6-dichlorodiphenylamine, 4-bromo-2-nitroaniline, 3,4-dichloroaniline, 2,6-dibromoaniline, 4-hexyloxyaniline, 4-bromo-2-fluoroacetanilide, 3,5-dinitroaniline, N-methyldiphenylamine, 4-fluoro-2-nitroacetanilide, 3-bromo-4-methylaniline, 3-tetrafluoroethoxyaniline, 2,5-dichloro-4-nitroaniline, 4-(N-BOC-aminomethyl)aniline, 2-bromo-N,N-dimethylaniline, 4-bromo-2-methyl-6-nitroaniline, 3-bromo-N,N-dimethylaniline, 4-bromo-3-methoxyaniline, 4-tert-butylaniline, 2,6-dibromo-4-nitroaniline, 2,4-dibromoaniline, 2-bromo-4-trifluoromethoxyaniline, 4-bromo-2-chloroaniline, 4-(difluoromethoxy)aniline, 4-octylaniline, 2,4-dimethylaniline, 2-bromo-5-methylaniline, 3-chloro-N-methylaniline, 2-bromo-5-(trifluoromethyl)aniline, 2,5-diethoxyaniline, 4-propylaniline, N,N-dimethyl-m-toluidine, N,N-diclohexylamine, 2,4-dichloroaniline, 4-nitrodiphenylamine, 2-fluoroacetanilide, 2-fluoro-4-nitroaniline, 4,4'-iminodianiline, m-nitroacetanilide, 2,5-bis(trifluoromethyl)aniline, N,N-dimethyl-o-toluidine, 3-methyldiphenylamine, 4-chloro-3-nitroaniline, 2-cyan-4-nitro-6-bromoaniline, 4,5-dimethyl-2-nitroaniline, 2-chloroaniline, 4-bromo-2-(trifluoromethoxy)aniline, 2-methyl-6-nitroaniline, 2-cyan-4-nitroaniline, N-nitrosodiphenylamine, 2-fluoro-5-nitroaniline, 4-bromo-3-(trifluoromethyl)aniline, 4-pentylaniline, 3-benzyloxyaniline, 5-chloro-2-iodoaniline, triphenylamine, 3,5-dichloroaniline, 2-bromo-4,6-dinitroaniline, 2,3-dichloroaniline, 4-iodo-2-methylaniline, 2,6-dichloroaniline, 4-heptylaniline, 4-bromoaniline, N-ethyl-m-toluidine, 4-bromo-o-phenylenediamine, N-methyl-1,2-phenylenediamine, 2-nitro-1,4-phenylenediamine, 4,5-dimethyl-1,2-phenylenediamine, 4,5-dichloro-1,2-phenylenediamine, N,N'-di-sec-butyl-p-phenylenediamine, 1,2-phenylenediamine, m-bromoaniline, 4-bromo-1-naphthylamine, (R)-(+)-1,1'-bi(2-naphthylamine), 1,2,3,4-tetrahydro-1-naphthylamine, 4-methoxy-m-phenylenediamine, 3-nitro-o-phenylenediamin, 2,4,6-trimethyl-1,3-phenylenediamine, 4-methyldiphenylamine, acetoacetyl-p-methoxyaniline, 2,6- difluoro-4-methoxyaniline, 2-methyl-3-nitroaniline, benzidine dihydrochloride, 2,6-dimethoxyaniline, 3,3'-dimethylbenzidine dihydrochloride, 5-chloro-2-nitrodiphenylamine, 3-(tert-butyl)aniline, acetoacet-o-carboxyanilide, 4-methylsulfonylaniline, 2-methyl-4-methoxy diphenylamine, N,N-dibutylaniline, 3-isopropylaniline, 4,4'-dimethyldiphenylamine, 4-methoxy-3-nitroaniline, o-benzylaniline, N,N-dihydroxyethyl-p-toluidine, 3,4-diethoxyaniline, 3,4,5-trichloroaniline, 5-bromo-4-fluoro-2-methylaniline, 4-octyloxyaniline, 2-bromo-3-methylaniline, 4,6-dimethyl-2-nitroaniline, 3,4-dichloro-N-methylaniline, 2'-bromoacetanilide, 4,6-dibromo-2,3-dichloroaniline, 4-bromo-2-ethylaniline, 4-bromo-N,N-diethylaniline, 3-phenoxyaniline, 4-fluoro-N-methylaniline, 2,6-diiodo-4-nitroaniline, 3-chloro-2,6-diethylaniline, 3-benzylaniline, 2-methoxy-N-methylaniline, 2-methoxy-6-methylaniline, 4-propoxyaniline, N-(4-methoxybenzylidene)aniline, 2-bromo-6-methyl-4-nitroaniline, 3-(N,N-diethyl)amino-4-methoxy acetanilide, 4-amino-N,N-dimethylaniline, N-acetanilide, 2,6-diethylaniline, 1,3-bis(aminomethyl)benzene, 3-hydroxy-N,N-diethylaniline, diaminotoluene, 4-dodecylaniline, N1-methyl-2,4-dichloroaniline, N-ethyl-2-nitroaniline, 4-tert-butyl-N,N-dimethylaniline, 4-trifluoromethyl-N-methylaniline, 4-tetradecylaniline, 4-butoxyacetanilide, 2,4,6-triphenylaniline, 2,6-diisopropyl-N,N-dimethylaniline, 3-chloro-4-(4-chlorophenoxy)aniline, 2-chloro-4,6-dimethylaniline, N-tert-butyl-3,5-dimethylaniline, 5,6,7,8-tetrahydro-2-naphthalenamine, 4-bromo-N-methylaniline, 3-iodo-4-methylaniline, 4-formamido-N-acetoacetanilide, N,N-diisopropylaniline, 4-aminostyrene, (R)-(+)-1,1'-bi(2-naphthylamine), 4-methoxy-2-naphthylamine, 4-benzyloxy-N-methylaniline, 3-bromo-N,N-diphenylaniline, 3-bromo-N-methylaniline, N-(tert-butoxycarbonyl)-3-bromoaniline, 2-bromo-N-methylaniline, N-(tert-butoxycarbonyl)-2-bromoaniline, 2,4,6-tri-tert-butyl-N-methylaniline, 4-octadecylaniline, 4-chloro-(N-boc)aniline, 2,4,6-tri-tert-butyl-N-(trimethylsilyl)aniline, 4'-ethyl-3'-methylacetanilide, N-ethyl-4-nitroaniline, 4-hexadecylaniline, 4-bromo-N,N-bis(trimethylsilyl)aniline, 2,5-di-tert-butylaniline, 2,4,6-trimethyl-N-methylaniline, N,N-hexylaniline, 3,3'-dichlorobenzidine, N-ethyl-N-isopropylaniline, 3-nitro-N-methylaniline, 4-iodo-3-nitroaniline, 4-benzyloxy-3-chloroaniline, 4-(4-bromophenoxy)aniline, 4-chloro-2,6-dinitroaniline, N,N-di-N-hexylaniline, 3,5-dimethyl-1,2-phenylenediamine, N,N-di-BOC-2-iodoaniline, N-methyl-4,4'-methylenedianiline, 4-[(trimethylsilyl)ethynyl]aniline, 4-bromo-2-ethylaniline, 2,6-difluoro-3-nitroaniline, methyl 4-(N-phenylcaramoyl)benzoate, 2-bromo-5-methylaniline, 5-bromo-4-fluoro-2-methylaniline, 4-isopropylaniline, diaminotoluene, 4,4'-iminodianiline, N,N-dimethylaniline, 2-methoxy-p-toluidine, 3-chloro-N,N-bis(trimethylsilyl)aniline, m-(o-toluidino)phenol, dichloroaniline, benzenedimethanamine, and the like.

A person skilled in the art can choose the appropriate aromatic amines according to the demands of industrial production.

The present invention can bring the advantages including: the present invention provides a method for preparing methyl acetate by the carbonylation of dimethyl ether on the H-type mordenite catalyst with adsorption of an organic amine, which improves the catalyst stability and prolongs the catalyst life through adding the organic amine in the feed gas to replenish/restrict the desorption of the organic amine from the catalyst during the reaction process.

Specific Embodiments of the Invention

In the examples, the calculation of percent conversion of dimethyl ether and selectivity of methyl acetate was based on the carbon mole number.

Percent conversion of dimethyl ether=[(the carbon mole number of dimethyl ether in the feed gas)−(the carbon mole number of dimethyl ether in the product)]÷(the carbon mole number of dimethyl ether in the feed gas)×(100%)

Selectivity of methyl acetate=(2/3)×(the carbon mole number of methyl acetate in the product)÷[(the carbon mole number of dimethyl ether in the feed gas)−(the carbon mole number of dimethyl ether in the product)]×(100%)

The present invention will be described in details by Examples, but the present invention is not limited to these Examples.

Comparative Example 1

50 g of H-type mordenite with the atom ratio of Si/Al=4:1 was calcinated in air at 550° C. for 5 hours in Muffle furnace, and then part of the powder sample was taken, pressed, crushed and sieved to 20-40 mesh sample used for the catalytic performance testing. 10 g of the sample was weighed and loaded into a stainless steel reaction tube with an internal diameter of 8.5 mm. The sample was activated at 300° C. for 1 hour under nitrogen gas at atmospheric pressure and the temperature was reduced to 250° C., and then the feed gas with a molar ratio of carbon monoxide to dimethyl ether of 15:1 was introduced and the pressure was increased to the reaction pressure of 2 MPa slowly and the gas hourly space velocity GHSV was controlled as 1000 h$^{-1}$. The reaction products were analyzed by an on-line gas chromatograph and the percent conversion of dimethyl ether and the selectivity of methyl acetate were calculated. The results were shown in Table 1.

Comparative Example 2

50 g of H-type mordenite with the atom ratio of Si/Al=4:1 was calcinated in air at 550° C. for 5 hours in Muffle furnace, and then part of the powder sample was taken, pressed, crushed and sieved to 20-40 mesh sample used for the catalytic performance testing. 10 g of the sample was weighed and loaded into a stainless steel reaction tube with an internal diameter of 8.5 mm. The sample was activated at 300° C. for 1 hour under nitrogen gas at atmospheric pressure, and then pyridine was blown into the sample by bubbling nitrogen gas in liquid pyridine. After be treated for 2 hours, the sample was purged by nitrogen gas for 1 hour and the temperature was reduced to 250° C., and then the feed gas with a molar ratio of carbon monoxide to dimethyl ether of 15:1 was introduced and the pressure was increased to the reaction pressure of 2 MPa slowly and the gas hourly space velocity GHSV was controlled as 1000 h$^{-1}$. The reaction products were analyzed by an on-line gas chromatograph and the percent conversion of dimethyl ether and the selectivity of methyl acetate were calculated. The results were shown in Table 1.

Comparative Example 3

The H-type mordenite in Comparative Example 1 was changed to the H-type mordenite with the atom ratio of Si/Al=6:1 and the rest experimental procedure was same as Comparative Example 1. The results were shown in Table 1.

Comparative Example 4

The H-type mordenite in Comparative Example 2 was changed to the H-type mordenite with the atom ratio of Si/Al=6:1 and the rest experimental procedure was same as Comparative Example 2. The results were shown in Table 1.

Comparative Example 5

The H-type mordenite in Comparative Example 1 was changed to the H-type mordenite with the atom ratio of Si/Al=60:1 and the rest experimental procedure was same as Comparative Example 1. The results were shown in Table 1.

Comparative Example 6

The H-type mordenite in Comparative Example 2 was changed to the H-type mordenite with the atom ratio of Si/Al=60:1 and pyridine adsorbed in the catalyst was changed to pyridine and 2-nitropyridine with the molar ratio of 1:1. The rest experimental procedure was same as Comparative Example 2 and the results were shown in Table 1.

Comparative Example 7

Pyridine adsorbed in the catalyst in Comparative Example 2 was changed to phenylamine. The rest experimental procedure was same as Comparative Example 2 and the results were shown in Table 1.

Comparative Example 8

Pyridine adsorbed in the catalyst in Comparative Example 4 was changed to phenylamine. The rest experimental procedure was same as Comparative Example 4 and the results were shown in Table 1.

Comparative Example 9

Pyridine and 2-nitropyridine with the molar ratio of 1:1 adsorbed in the catalyst in Comparative Example 6 were changed to phenylamine and 4-ethylaniline with the molar ratio of 1:1. The rest experimental procedure was same as Comparative Example 6 and the results were shown in Table 1.

Comparative Example 10

Pyridine adsorbed in the catalyst in Comparative Example 2 was changed to

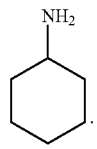

The rest experimental procedure was same as Comparative Example 2 and the results were shown in Table 1.

Comparative Example 11

Pyridine adsorbed in the catalyst in Comparative Example 4 was changed to

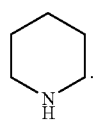

The rest experimental procedure was same as Comparative Example 4 and the results were shown in Table 1.

Comparative Example 12

Pyridine and 2-nitropyridine with the molar ratio of 1:1 adsorbed in the catalyst in Comparative Example 6 were changed to

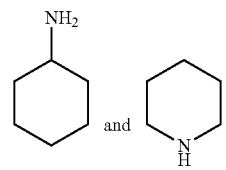

with the molar ratio of 1:1. The rest experimental procedure was same as Comparative Example 6 and the results were shown in Table 1.

Example 1

50 g of H-type mordenite with the atom ratio of Si/Al=4:1 was calcinated in air at 550° C. for 5 hours in Muffle furnace, and then part of the powder sample was taken, pressed, crushed and sieved to 20-40 mesh sample used for the catalytic performance testing. 10 g of the sample was weighed and loaded into a stainless steel reaction tube with an internal diameter of 8.5 mm. The sample was activated at 300° C. for 1 hour under nitrogen gas at atmospheric pressure, and then pyridine was blown into the sample by bubbling nitrogen gas in liquid pyridine. After be treated for 2 hours, the sample was purged by nitrogen gas for 1 hour and the temperature was reduced to 250° C., and then the feed gas with a molar ratio of carbon monoxide:dimethyl ether:pyridine=15:1:0.001 was introduced and the pressure was increased to the reaction pressure of 2 MPa slowly and the gas hourly space velocity GHSV was controlled as 1000 $h^{-1}$. The reaction products were analyzed by an on-line gas chromatograph and the percent conversion of dimethyl ether and the selectivity of methyl acetate were calculated. The results were shown in Table 1.

Example 2

The experimental procedure was same as Example 1, except that the H-type mordenite was changed to the H-type mordenite with the atom ratio of Si/Al=6:1, and pyridine adsorbed in the catalyst was changed to 2,3-dichloro-5-(trifluoromethyl)pyridine, and pyridine in the feed gas was changed to 2-fluoropyridine. The rest experimental procedure was same as Example 1 and the results were shown in Table 1.

Example 3

The experimental procedure was same as Example 1, except that the H-type mordenite was changed to the H-type mordenite with the atom ratio of Si/Al=60:1, and pyridine adsorbed in the catalyst was changed to 2-iodopyridine, and pyridine in the feed gas was changed to 2-bromopyridine and 2-chloropyridine with the molar ratio of 1:1. The rest experimental procedure was same as Example 1 and the results were shown in Table 1.

Example 4

The feed gas in Example 1 was changed to a feed gas with the molar ratio of carbon monoxide:dimethyl ether:2-methylpyridine=15:1:0.0001 and the reaction pressure was changed to 0.1 MPa and the gas hourly space velocity GHSV was changed to 500 h$^{-1}$. The rest experimental procedure was same as Example 1 and the results were shown in Table 1.

Example 5

Pyridine adsorbed in the catalyst in Example 1 was changed to 2-ethylpyridine and the feed gas was changed to a feed gas with the molar ratio of carbon monoxide:hydrogen gas:dimethyl ether:pyridine=1:10:1:0.01, and the reaction temperature was changed to 320° C., and the reaction pressure was changed to 8 MPa, and the gas hourly space velocity GHSV was changed to 10000 h$^{-1}$. The rest experimental procedure was same as Example 1 and the results were shown in Table 1.

Example 6

Pyridine adsorbed in the catalyst in Example 1 was changed to 2-methylpyridine and the feed gas was changed to a feed gas with the molar ratio of carbon monoxide:hydrogen gas:dimethyl ether:2-chloropyridine=45:20:1:0.2 and the reaction temperature was changed to 150° C. The rest experimental procedure was same as Example 1 and the results were shown in Table 1.

Example 7

50 g of H-type mordenite with the atom ratio of Si/Al=4:1 was calcinated in air at 550° C. for 5 hours in Muffle furnace, and then part of the powder sample was taken, pressed, crushed and sieved to 20-40 mesh sample used for the catalytic performance testing. 10 g of the sample was weighed and loaded into a stainless steel reaction tube with an internal diameter of 8.5 mm. The sample was activated at 300° C. for 1 hour under nitrogen gas at atmospheric pressure, and then phenylamine was blown into the sample by bubbling nitrogen gas in liquid phenylamine. After be treated for 2 h, the sample was purged by nitrogen gas for 1 h and the temperature was reduced to 250° C., and then the feed gas with a molar ratio of carbon monoxide:dimethyl ether:phenylamine=15:1:0.001 was introduced and the pressure was increased to the reaction pressure of 2 MPa slowly and the gas hourly space velocity GHSV was controlled as 1000 h$^{-1}$. The reaction products were analyzed by an on-line gas chromatograph and the percent conversion of dimethyl ether and the selectivity of methyl acetate were calculated. The results were shown in Table 1.

Example 8

The experimental procedure was same as Example 7, except that the H-type mordenite was changed to the H-type mordenite with the atom ratio of Si/Al=6:1, and phenylamine adsorbed in the catalyst was changed to 2,6-dichloro-4-(trifluoromethyl)aniline, and the feed gas was changed to a feed gas with the molar ratio of carbon monoxide:dimethyl ether:4-fluoroaniline=15:1:0.00001. The rest experimental procedure was same as Example 7 and the results were shown in Table 1.

Example 9

The experimental procedure was same as Example 7, except that the H-type mordenite was changed to the H-type mordenite with the atom ratio of Si/Al=60:1, and phenylamine adsorbed in the catalyst was changed to N,N-dimethyl-p-toluidine, and phenylamine in the feed gas was changed to 2-bromoaniline and 3-chloroaniline with the molar ratio of 1:1. The rest experimental procedure was same as Example 7 and the results were shown in Table 1.

Example 10

The feed gas in Example 7 was changed to a feed gas with the molar ratio of carbon monoxide:dimethyl ether:4-methylaniline=15:1:0.0001, and the reaction pressure was changed to 0.1 MPa, and the gas hourly space velocity GHSV was changed to 500 h$^{-1}$. The rest experimental procedure was same as Example 7 and the results were shown in Table 1.

Example 11

Phenylamine adsorbed in the catalyst in Example 7 was changed to 2-ethylaniline, and the feed gas was changed to a feed gas with the molar ratio of carbon monoxide:hydrogen gas:dimethyl ether:phenylamine=1:10:1:0.01, and the reaction temperature was changed to 320° C., and the reaction pressure was changed to 8 MPa, and the gas hourly space velocity GHSV was changed to 10000 h$^{-1}$. The rest experimental procedure was same as Example 7 and the results were shown in Table 1.

Example 12

Phenylamine adsorbed in the catalyst in Example 7 was changed to 4-methylaniline, and the feed gas was changed to a feed gas with the molar ratio of carbon monoxide:hydrogen gas:dimethyl ether:2-chloroaniline=45:20:1:0.2, and the reaction temperature was changed to 150° C. The rest experimental procedure was same as Example 7 and the results were shown in Table 1.

Example 13

50 g of H-type mordenite with the atom ratio of Si/Al=4:1 was calcinated in air at 550° C. for 5 hours in Muffle furnace, and then part of the powder sample was taken, pressed, crushed and sieved to 20-40 mesh sample used for the catalytic performance testing. 10 g of the sample was weighed and loaded into a stainless steel reaction tube with an internal diameter of 8.5 mm. The sample was activated at 300° C. for 1 hour under nitrogen gas at atmospheric pressure, and then

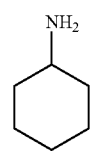

was blown into the sample by bubbling nitrogen gas in liquid

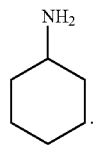

After be treated for 2 h, the sample was purged by nitrogen gas for 1 h and the temperature was reduced to 250° C., and then the feed gas with a molar ratio of carbon monoxide:dimethyl ether:

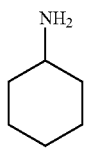

=15:1:0.001 was introduced and the pressure was increased to the reaction pressure of 2 MPa slowly and the gas hourly space velocity GHSV was controlled as 1000 h$^{-1}$. The reaction products were analyzed by an on-line gas chromatograph and the percent conversion of dimethyl ether and the selectivity of methyl acetate were calculated. The results were shown in Table 1.

Example 14

The experimental procedure was same as Example 13, except that the H-type mordenite was changed to the H-type mordenite with the atom ratio of Si/Al=6:1, and the alicyclic amine adsorbed in the catalyst was changed to

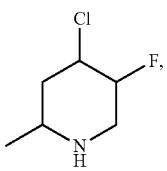

and the alicyclic amine in the feed gas was changed to

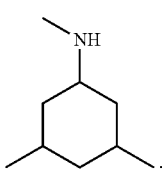

The rest experimental procedure was same as Example 13 and the results were shown in Table 1.

Example 15

The experimental procedure was same as Example 13, except that the H-type mordenite was changed to the H-type mordenite with the atom ratio of Si/Al=60:1, and the alicyclic amine adsorbed in the catalyst was changed to

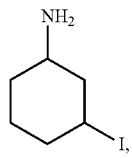

and the alicyclic amine in the feed gas was changed to

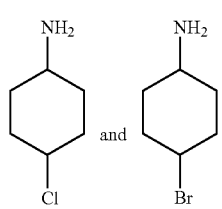

with the molar ratio of 1:1. The rest experimental procedure was same as Example 13 and the results were shown in Table 1.

Example 16

The feed gas in Example 13 was changed to a feed gas with the molar ratio of carbon monoxide:dimethyl ether:

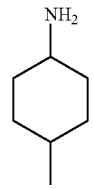

=15:1:0.0001, and the reaction pressure was changed to 0.1 MPa, and the gas hourly space velocity GHSV was changed to 500 h$^{-1}$. The rest experimental procedure was same as Example 13 and the results were shown in Table 1.

Example 17

The alicyclic amine adsorbed in the catalyst in Example 13 was changed to

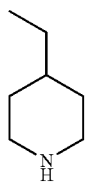

and the feed gas was changed to a feed gas with the molar ratio of carbon monoxide:hydrogen gas:dimethyl ether:

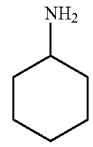

=1:10:1:0.01, and the reaction temperature was changed to 320° C., and the pressure was increased to the reaction pressure of 8 MPa slowly and the gas hourly space velocity GHSV was controlled as 10000 h⁻¹. The rest experimental procedure was same as Example 13 and the results were shown in Table 1.

Example 18

The alicyclic amine adsorbed in the catalyst in Example 13 was changed to

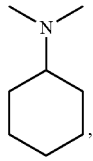

and the feed gas was changed to a feed gas with the molar ratio of carbon monoxide:hydrogen gas:dimethyl ether:

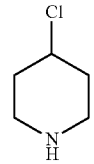

=45:20:1:0.2, and the reaction temperature was changed to 150° C. The rest experimental procedure was same as Example 13 and the results were shown in Table 1.

TABLE 1

Reaction conditions and the results of Comparative Examples and Examples

| Comparative Example/Example | Atom ratio of Si:Al of the catalyst/the organic amine adsorbed in the catalyst | Composition and molar ratio of the feed gas | Raction temperature pressure GHSV | Reaction time (hour) | Percent conversion of dimethyl ether (%) | Selectivity of methyl acetate (%) |
|---|---|---|---|---|---|---|
| Comparative Example 1 | 4:1/- | carbon monoxide: dimethyl ether = 15:1 | 250° C. 2 MPa 1000 h⁻¹ | 2 8 30 | 65.8 32.3 1.5 | 99.1 96.3 89.0 |
| Comparative Example 2 | 4:1/pyridine | carbon monoxide: dimethyl ether = 15:1 | 250° C. 2 MPa 1000 h⁻¹ | 100 200 300 | 54.9 48.7 12.1 | 99.6 99.1 97.6 |
| Comparative Example 3 | 6:1/- | carbon monoxide: dimethyl ether = 15:1 | 250° C. 2 MPa 1000 h⁻¹ | 2 8 30 | 66.9 35.7 2.1 | 99.5 97.2 90.1 |
| Comparative Example 4 | 6:1/pyridine | carbon monoxide: dimethyl ether = 15:1 | 250° C. 2 MPa 1000 h⁻¹ | 100 200 300 | 60.2 50.7 15.1 | 99.7 99.2 98.0 |
| Comparative Example 5 | 60:1/- | carbon monoxide: dimethyl ether = 15:1 | 250° C. 2 MPa 1000 h⁻¹ | 2 8 30 | 51.1 27.1 0.3 | 98.1 94.7 80.0 |
| Comparative Example 6 | 60:1/pyridine and 2-nitropyridine with the molar ratio of 1:1 | carbon monoxide: dimethyl ether = 15:1 | 250° C. 2 MPa 1000 h⁻¹ | 100 200 300 | 44.1 39.7 9.1 | 99.3 99.0 95.2 |
| Comparative Example 7 | 4:1/phenylamine | carbon monoxide: dimethyl ether = 15:1 | 250° C. 2 MPa 1000 h⁻¹ | 100 200 300 | 51.3 46.7 10.0 | 99.5 99.0 96.6 |
| Comparative Example 8 | 6:1/phenylamine | carbon monoxide: dimethyl ether = 15:1 | 250° C. 2 MPa 1000 h⁻¹ | 100 200 300 | 57.2 52.7 14.1 | 99.4 98.2 97.0 |
| Comparative Example 9 | 60:1/phenylamine and 4-ethylaniline with the molar ratio of 1:1 | carbon monoxide: dimethyl ether = 15:1 | 250° C. 2 MPa 1000 h⁻¹ | 100 200 300 | 41.1 38.7 8.2 | 99.1 98.0 94.2 |
| Comparative Example 10 | 4:1/cyclohexylamine | carbon monoxide: dimethyl ether = 15:1 | 250° C. 2 MPa 1000 h⁻¹ | 100 200 300 | 44.9 40.7 15.1 | 99.3 99.1 97.0 |
| Comparative Example 11 | 6:1/piperidine | carbon monoxide: dimethyl ether = 15:1 | 250° C. 2 MPa 1000 h⁻¹ | 100 200 300 | 57.2 52.7 13.1 | 99.5 99.1 98.2 |

TABLE 1-continued

Reaction conditions and the results of Comparative Examples and Examples

| Comparative Example/ Example | Atom ratio of Si:Al of the catalyst/the organic amine adsorbed in the catalyst | Composition and molar ratio of the feed gas | Raction temperature pressure GHSV | Reaction time (hour) | Percent conversion of dimethyl ether (%) | Selectivity of methyl acetate (%) |
|---|---|---|---|---|---|---|
| Comparative Example 12 | 60:1/ 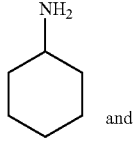 and 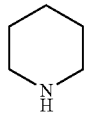 with the molar ratio of 1:1 | carbon monoxide: dimethyl ether = 15:1 | 250° C. 2 MPa 1000 h$^{-1}$ | 100 200 300 | 41.1 39.6 8.1 | 99.6 99.0 94.2 |
| Example 1 | 4:1/pyridine | carbon monoxide: dimethyl ether: pyridine = 15:1:0.001 | 250° C. 2 MPa 1000 h$^{-1}$ | 100 400 1000 | 54.3 54.1 50.9 | 99.8 99.5 99.1 |
| Example 2 | 6:1/ 2,3-dichloro-5-(trifl uoromethyl)pyridine | carbon monoxide: dimethyl ether: 2-fluoropyridine = 15:1:0.001 | 250° C. 2 MPa 1000 h$^{-1}$ | 100 400 1000 | 59.4 59.2 52.9 | 99.8 99.4 99.0 |
| Example 3 | 60:1/ 2-iodopyridine | carbon monoxide: dimethyl ether: 2-bromopyridine: 2-chloropyridine = 15:1:0.0005:0.0005 | 250° C. 2 MPa 1000 h$^{-1}$ | 100 400 1000 | 43.6 42.0 39.9 | 99.7 99.3 98.9 |
| Example 4 | 4:1/pyridine | carbon monoxide: dimethyl ether: 2-methylpyridine = 15:1:0.0001 | 250° C. 0.1 MPa 500 h$^{-1}$ | 100 400 1000 | 53.8 53.0 51.2 | 99.7 99.4 99.0 |
| Example 5 | 4:1/ 2-ethylpyridine | carbon monoxide: hydrogen gas: dimethyl ether: pyridine = 1:10:1:0.01 | 320° C. 8 MPa 10000 h$^{-1}$ | 100 400 1000 | 45.1 43.2 38.2 | 99.6 98.9 97.0 |
| Example 6 | 4:1/ 2-methylpyridine | carbon monoxide: hydrogen gas: dimethyl ether: 2-chloropyridine = 45:20:1:0.2 | 150° C. 2 MPa 1000 h$^{-1}$ | 100 400 1000 | 37.3 36.2 34.9 | 99.4 99.3 99.0 |
| Example 7 | 4:1/phenylamine | carbon monoxide: dimethyl ether: phenylamine = 15:1:0.001 | 250° C. 2 MPa 1000 h$^{-1}$ | 100 400 1000 | 52.7 50.2 48.9 | 99.2 98.5 98.1 |
| Example 8 | 6:1/ 2,6-dichloro-4-(tri- fluoromethyl)aniline | carbon monoxide: dimethyl ether: 4-fluoroaniline = 15:1:0.00001 | 250° C. 2 MPa 1000 h$^{-1}$ | 100 400 1000 | 54.3 52.2 50.9 | 99.6 99.1 989.7 |
| Example 9 | 60:1/ N,N-dimethyl-p-tol- uidine | carbon monoxide: dimethyl ether: 2-bromaniline: 3-chloroaniline = 15:1:0.0005:0.0005 | 250° C. 2 MPa 1000 h$^{-1}$ | 100 400 1000 | 40.6 39.0 36.9 | 99.6 99.0 97.9 |
| Example 10 | 4:1/phenylamine | carbon monoxide: dimethyl ether: 4-methylaniline = 15:1:0.0001 | 250° C. 0.1 MPa 500 h$^{-1}$ | 100 400 1000 | 43.7 43.0 41.3 | 99.7 99.2 98.0 |
| Example 11 | 4:1/2-ethylaniline | carbon monoxide: hydrogen gas: dimethyl ether: phenylamine = 1:10:1:0.01 | 320° C. 8 MPa 10000 h$^{-1}$ | 100 400 1000 | 45.8 43.5 37.2 | 99.7 98.6 97.4 |

TABLE 1-continued

Reaction conditions and the results of Comparative Examples and Examples

| Comparative Example/ Example | Atom ratio of Si:Al of the catalyst/the organic amine adsorbed in the catalyst | Composition and molar ratio of the feed gas | Raction temperature pressure GHSV | Reaction time (hour) | Percent conversion of dimethyl ether (%) | Selectivity of methyl acetate (%) |
|---|---|---|---|---|---|---|
| Example 12 | 4:1/ 4-methylaniline | carbon monoxide hydrogen gas: dimethyl ether: 2-chloroaniline = 45:20:1:0.2 | 150° C. 2 MPa 1000 h$^{-1}$ | 100 400 1000 | 35.3 33.2 32.9 | 99.1 98.9 98.0 |
| Example 13 | 4:1/ 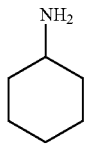 | carbon monoxide: dimethyl ether: 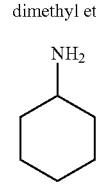 = 15:1: 0.001 | 250° C. 2 MPa 1000 h$^{-1}$ | 100 400 1000 | 44.3 39.1 38.9 | 99.4 98.5 98.1 |
| Example 14 | 6:1/ 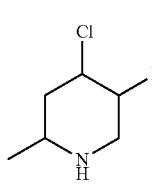 | carbon monoxide: dimethyl ether: 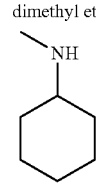 = 15:1: 0.001 | 250° C. 2 MPa 1000 h$^{-1}$ | 100 400 1000 | 59.8 56.2 51.9 | 99.7 99.2 99.0 |
| Example 15 | 60:1/ 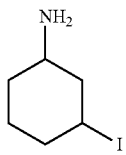 | carbon monoxide: dimethyl ether: 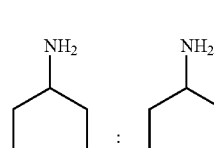 : 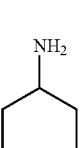 = 15:1:0.0005:0.0005 | 250° C. 2 MPa 1000 h$^{-1}$ | 100 400 1000 | 43.5 41.0 37.9 | 99.6 99.3 97.9 |
| Example 16 | 4:1/ 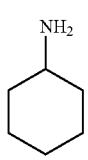 | carbon monoxide: dimethyl ether: 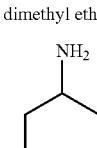 = 15:1:0.0001 | 250° C. 0.1 MPa 500 h$^{-1}$ | 100 400 1000 | 55.8 52.6 49.2 | 99.8 99.2 98.9 |

TABLE 1-continued

Reaction conditions and the results of Comparative Examples and Examples

| Comparative Example/ Example | Atom ratio of Si:Al of the catalyst/the organic amine adsorbed in the catalyst | Composition and molar ratio of the feed gas | Raction temperature pressure GHSV | Reaction time (hour) | Percent conversion of dimethyl ether (%) | Selectivity of methyl acetate (%) |
|---|---|---|---|---|---|---|
| Example 17 | 4:1/ 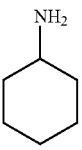 | carbon monoxide: hydrogen gas: dimethyl: 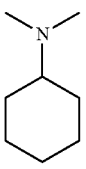 = 1:10:1:0.01 | 320° C. 8 MPa 10000 h⁻¹ | 100 400 1000 | 44.1 40.2 37.2 | 99.3 98.6 97.4 |
| Example 18 | 4:1/ 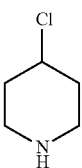 | carbon monoxide: hydrogen gas: dimethyl ether:  = 45:20:1:0.2 | 150° C. 2 MPa 1000 h⁻¹ | 100 400 1000 | 35.3 33.1 32.8 | 99.7 98.9 98.0 |

The invention claimed is:

1. A method for preparing methyl acetate, in which a feed gas containing an organic amine, dimethyl ether, carbon monoxide and optional hydrogen gas goes through a reaction region loaded with a H-type mordenite catalyst, to produce methyl acetate at a reaction temperature range from 150° C. to 320° C., a reaction pressure range from 0.1 MPa to 8 MPa and a gas hourly space velocity range from 500h-1 to 10000h-1;
wherein said H-type mordenite catalyst is a H-type mordenite catalyst with adsorption of an organic amine;
in said feed gas, the molar ratio range of carbon monoxide to dimethyl ether is from 1:1 to 45:1, and the molar ratio range of the organic amine to dimethyl ether is from 0.00001:1 to 0.2:1, and the molar ratio range of hydrogen gas to dimethyl ether is from 0:1 to 20:1;
said reaction region contains one reactor or reactors which are connected in series or in parallel;
said organic amine is at least one selected from pyridines amines, aromatic amines or alicyclic amines.

2. A method for preparing methyl acetate according to claim 1, wherein in said feed gas, the molar ratio range of the organic amine to dimethyl ether is from 0.0001:1 to 0.01:1.

3. A method for preparing methyl acetate according to claim 1, wherein said H-type mordenite catalyst with adsorption of an organic amine is prepared by the steps as follows:
the H-type mordenite is loaded in a reactor, and then at an adsorption temperature range from 90° C. to 420° C., a mixture gas is introduced into the reactor, which contains the organic amine and at least one selected from carbon monoxide, hydrogen gas, air, nitrogen gas, helium gas or argon gas; after the saturated adsorption of the organic amine, the reactor is purged by at least one selected from carbon monoxide, hydrogen gas, air, nitrogen gas, helium gas or argon gas for a time range from 0.5 hour to 6 hours at the adsorption temperature, to obtain said H-type mordenite catalyst with adsorption of the organic amine.

4. A method for preparing methyl acetate according to claim 1, wherein the atom ratio of silicon to aluminum in said H-type mordenite catalyst is at a range from 4:1 to 60:1.

5. A method for preparing methyl acetate according to claim 1, wherein said pyridines amine is at least one selected from pyridine or the substituted pyridines said aromatic amine is at 8 or the substituted alicyclic amines with the number of ring members ranging from 5 to 8; preferably, said alicyclic amine is at least one selected from cyclohexylamine, piperidine, the substituted cyclohexylamines or the substituted piperidines.

6. A method for preparing methyl acetate according to claim 5, wherein said substituted pyridines are the compounds which one, two or three of five H atoms in the pyridine ring is respectively substituted by the substituent group selected from F, Cl, Br, I, $CH_3$, $CF_3$, $CH_3CH_2$ or $NO_2$; said substituted phenylamines are the compounds which one, two, three, four, five, six or seven of seven H atoms composed of five H atoms in the benzene ring and two atoms in the amine group is respectively substituted by the substituent group selected from F, Cl, Br, I, $CH_3$, $CF_3$ or $CH_3CH_2$; said substituted cyclohexylamines are the compounds which at least one of thirteen H atoms in the cyclohexylamine is respectively substituted by the substituent group selected from F, Cl, Br, I, $CH_3$, $CF_3$, $CH_3CH_2$ or $NO_2$; said substituted piperidines are the compounds which at least one of eleven H atoms in the piperidine is respectively substituted by the substituent group selected from F, Cl, Br, I, $CH_3$, $CF_3$, $CH_3CH_2$ or $NO_2$.

7. A method for preparing methyl acetate according to claim 1, wherein the organic amine adsorbed in said catalyst is same as the organic amine in said feed gas, or the organic amine adsorbed in said catalyst is different from the organic amine in said feed gas.

8. A method for preparing methyl acetate according to claim 1, wherein the organic amine adsorbed in said catalyst is at least one selected from pyridine, 2-methylpyridine, phenylamine, 4-methylaniline, cyclohexylamine or piperidine; the organic amine in said feed gas is at least one selected from pyridine, 2-methylpyridine, phenylamine, 4-methylaniline, cyclohexylamine or piperidine.

9. A method for preparing methyl acetate according to claim 1, wherein the organic amine in said feed gas is the fresh organic amine or the recycled organic amine obtained in the process of the product separation.

10. A method for preparing methyl acetate according to claim 1, wherein said reactor is a continuous flow fixed bed reactor, a moving bed reactor or a fluid bed reactor.

11. The method for preparing methyl acetate according to claim 3, wherein the adsorption temperature range is from 160° C. to 320° C.

12. A method for preparing methyl acetate according to claim 5, wherein said alicyclic amine is at least one selected from cyclohexylamine, piperidine, the substituted cyclohexylamines or the substituted piperidines.

* * * * *

UNITED STATES PATENT AND TRADEMARK OFFICE
CERTIFICATE OF CORRECTION

PATENT NO. : 9,440,226 B2
APPLICATION NO. : 14/650589
DATED : September 13, 2016
INVENTOR(S) : Youming Ni et al.

Page 1 of 1

It is certified that error appears in the above-identified patent and that said Letters Patent is hereby corrected as shown below:

In the Claims

Claim 5, Column 2, Line 44, please delete "; preferably, said acrylic amine is at least one selected from cyclohexylamine, piperidine, the substituted cyclohexylamines or the substituted piperidines."

Signed and Sealed this
Fifteenth Day of November, 2016

Michelle K. Lee
*Director of the United States Patent and Trademark Office*